US00PP16686P2

(12) United States Plant Patent
Utecht

(10) Patent No.: US PP16,686 P2
(45) Date of Patent: Jun. 20, 2006

(54) *GERANIUM* PLANT NAMED 'FISWIPINK'

(50) Latin Name: *Pelargonium peltatum L'Héritier (hybrid)*
Varietal Denomination: Fiswipink

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 90 days.

(21) Appl. No.: 10/998,668

(22) Filed: Nov. 30, 2004

(51) **Int. Cl.*A01H 5/00***
(2006.01)

(52) U.S. Cl. ..... Plt./332

(58) Field of Classification Search ..... Plt./332
See application file for complete search history.

(56) References Cited

PUBLICATIONS

GTITM UPOVROM Citation for 'Fiswipink' as per DE PBR PEL 01542; Jun. 29, 1999.*

GTITM UPOVROM Citation for 'Fiswipink' as per QZ PBR 001048; Jul. 10, 2000.*

German PBR Application No. PEL 1542 filed Jun. 29, 1999, granted Nov. 6, 2000, and protection terminated Dec. 6, 2000 (Copy of German Gazettes dated 1) Aug. 15, 1999—Listing Assigned Application for Protection Number (2 pgs), 2) Sep. 15, 2000—Publishing Proposed Variety Denomination (2 pgs), 3) Dec. 15, 2000—Publishing Grant of Protection, and 4) Jan. 15, 2001—Publishing Termination of Protection (2 pgs)).

Canadian PBR Application No. 03–3926 filed Dec. 10, 2003 (Copy of Canadian Plant Varieties Journal dated Apr., 2004 Listing Assigned Application Number (2 pgs).

Community Plant Variety Office (CPVO) No. 2000/1048 filed Jul. 10, 2000 (Copy of Official Gazette of th CPVO dated 1) Oct. 16, 2000 Listing Assigned Application Number and Variety Denomination (3 pgs), 2) Dec. 15, 2000—Publishing Variety Denomination, and 3) Dec. 15, 2001—Publishing Grant of Protection (2 pgs)).

Fischer 2005 catalogue offering 'Fiswipink' (with shipment of plant material available starting Dec., 2004) (3 pgs).

* cited by examiner

*Primary Examiner*—Kent L. Bell
(74) *Attorney, Agent, or Firm*—Foley & Lardner LLP

(57) ABSTRACT

A new and distinct cultivar of *geranium* plant named 'Fiswipink', particularly characterized by the combined features of large, pink, semi-double to double flowers; compact, semi-spherically shaped inflorescences with relatively many individual flowers; medium green foliage with distinct lobes and distinct zonation; medium growth vigor; initially round and bushy, and later weakly trailing plant habit; early spring flowering response and continuous flowering throughout the summer.

1 Drawing Sheet

Genus and species of the plant claimed: *Pelargonium peltatum L'Héritier* (hybrid).
Variety denomination: 'Fiswipink'.

BACKGROUND OF THE INVENTION

The present invention comprises a new and distinct cultivar of *geranium*, botanically known as *Pelargonium peltatum,* and hereinafter referred to by the cultivar name 'Fiswipink'.

'Fiswipink' is a product of a planned breeding program which had the objective of creating new ivy *geranium* cultivars with semi-double to double flower type, zoned foliage, and about medium sized, well-branched growth habit, in various flower colors.

'Fiswipink' originated from a hybridization made by the inventor, Angelika Utecht, in a controlled breeding program in Hillscheid, Germany, in 1997. The female parent was an unpatented plant, no. 93-361-22, having red, double flowers, medium green foliage with slight zonation, vigorous growth and trailing plant habit. The male parent of 'Fiswipink' was the unpatented hybrid plant no. 94-1793-10, which was characterized by red, single-type flowers, foliage with relatively strong zonation, and about medium growth habit.

'Fiswipink' was selected as one flowering plant within the progeny of the stated cross by Angelika Utecht in 1998 in a controlled environment in Moncarapacho, Portugal.

The first act of asexual reproduction of 'Fiswipink' was accomplished when vegetative cuttings were taken from the initial selection in the fall of 1998 in a controlled environment in Moncarapacho, Portugal, by, or under the supervision of, Angelika Utecht.

Horticultural examination of plants grown from cuttings of the plant initiated in May of 1999 in Hillscheid, Germany, and continuing thereafter, has demonstrated that the combination of characteristics as herein disclosed for 'Fiswipink' are firmly fixed and are retained through successive generations of asexual reproduction.

BRIEF SUMMARY OF THE INVENTION

'Fiswipink' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fiswipink' in combination distinguish this *geranium* as a new and distinct cultivar:

1. vary large, pink, semi-double to double flowers;
2. compact, semi-spherically shaped inflorescences with relatively many flowers;
3. medium green foliage with distinct lobes, and with distinct zonation;
4. medium vigor, round and bushy plant habit with short, trailing branches; and
5. early spring flowering response.

Of the many commercial cultivars known to the present inventor, the most similar are the varieties 'Guimongol' (U.S. Plant Pat. No. 9,352) and 'Freestyle Pink II' (U.S. Plant Pat. No. 14,524).

In comparison to 'Guimongol', 'Fiswipink' has a somewhat deeper and slightly more bluish hue of pink flower color. 'Fiswipink' begins flowering early, too, but its flowers hardly tend to be "shattering" (easily dropping of petals). Additionally, plant habit of 'Fiswipink' is similarly round, but considerably taller.

In comparison to the deeper, salmon-pink colored flowers of 'Freestyle Pink II', 'Fiswipink' has larger flowers and inflorescence of a somewhat lighter and more bluish-pink hue. Furthermore, the leaves of 'Fiswipink' are ivy-shaped with pointed lobes, while those of 'Freestyle Pink II' have flatter leaf blades with rounded lobes and somewhat stronger zonation. Additionally, plant habit of 'Freestyle Pink II' develops longer, trailing branches.

BRIEF DESCRIPTION OF THE DRAWINGS

The accompanying photographic drawing shows typical flower and foliage characteristics of 'Fiswipink' with colors being as true as possible with an illustration of this type. The photographic drawing shows as FIG. 1 a close-up view of a branched end of 'Fiswipink' with leaves, buds and inflorescences; and as FIG. 2 a side perspective view of a flowering potted 'Fiswipink' with leaves, buds and inflorescences.

DETAILED BOTANICAL DESCRIPTION

Figure 1:
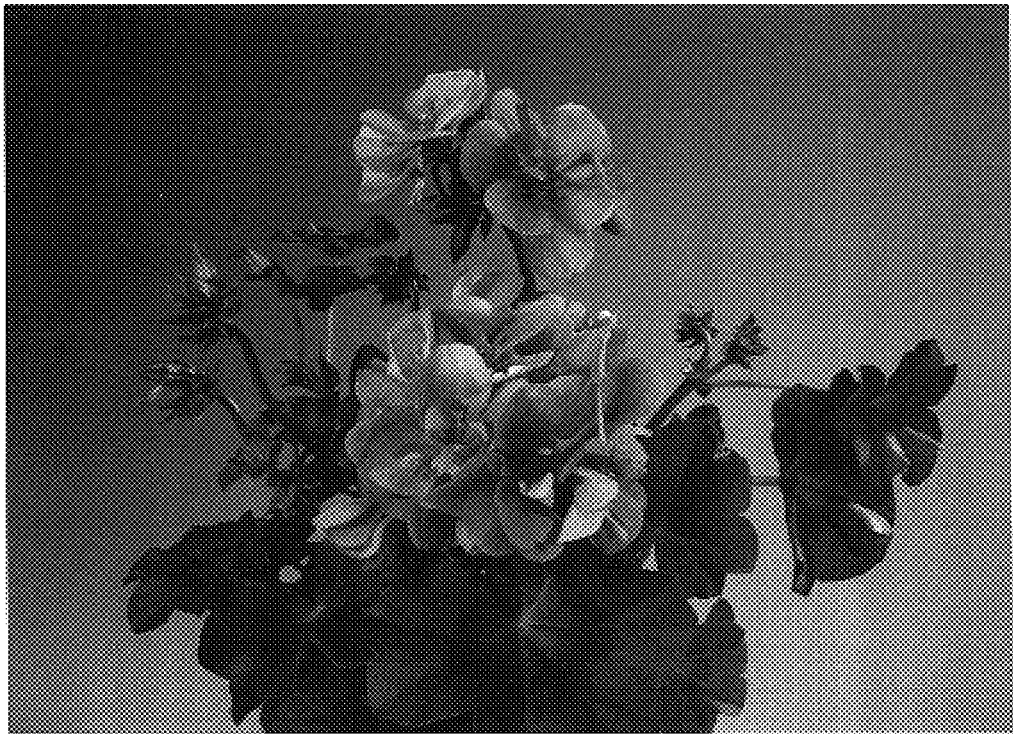
Figure 2:
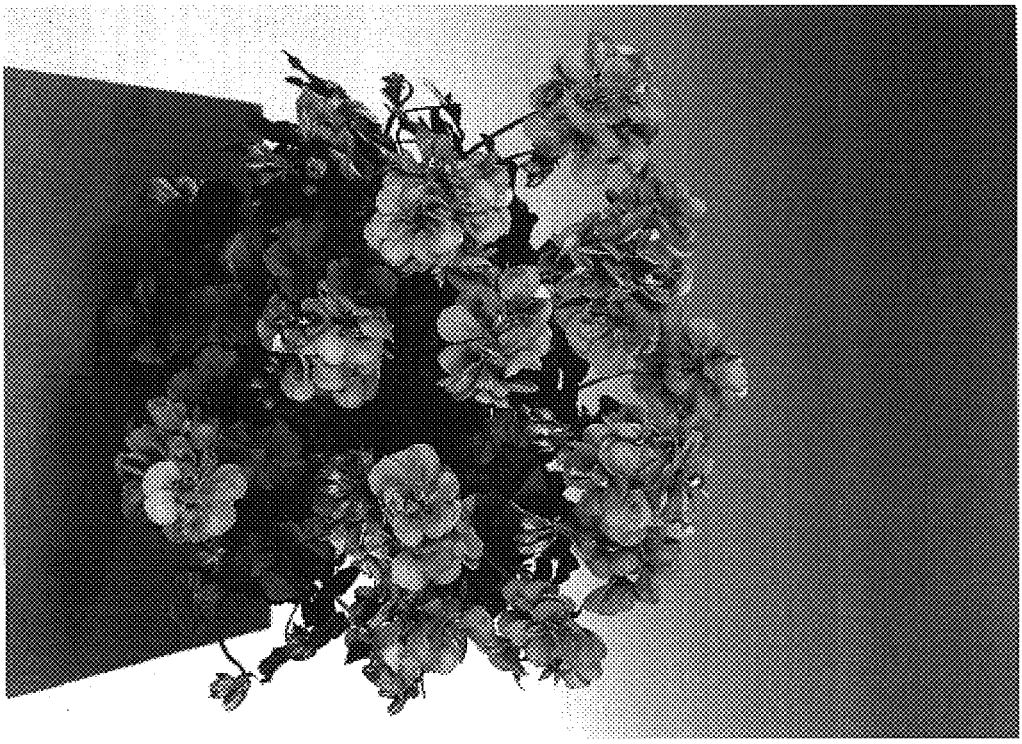

The measurements were taken in Hillscheid, Germany, in mid May 2003, 15 weeks after planting of rooted cuttings. The plants were growing in 14 cm pots; they had been pinched once.

In the following description, color references are made to The Royal Horticultural Society Color Chart. The color values were determined indoors from plants growing in a green-house in May 2003, in Hillscheid, Germany.

Parentage:
- *Male parent.*—Unpatented, hybrid plant no 94-1793-10.
- *Female parent.*—Unpatented, hybrid plant no. 93-361-22.

Classification: *Pelargonium peltatum L'Héritier* (hybrid).
Propagation: Vegetative cuttings.
Inflorescence:
Umbel:
- *Shape.*—Semi-spherical.
- *Average diameter.*—88 mm.
- *Average depth.*—55–65 mm.
- *Numbers of flowers per umbel.*—About 12–15.

Peduncle:
- *Peduncle length.*—133 mm.
- *Peduncle diameter.*—Mostly 3 mm, occasionally up to 4 mm.
- *Peduncle color.*—Light green, RHS 143 C.

Pedicel:
- *Pedicel length.*—23 mm in length, occasionally with a spur.
- *Pedicel diameter.*—2 mm.
- *Pedical color.*—Light green, RHS 143 B, partly brown (greyed-red), RHS 179 A.

Corolla:
- *Average length.*—60 mm.
- *Average width.*—51 mm.
- *Depth.*—15 to 20 mm.
- *Form.*—Semi-double to double type.
- *Shape.*—Zygomorphic, often with a gap between upper and lower petals, aspect of the petals somewhat irregular, horizontally to upright directed.

Petaloids:
- *Number of petaloids.*—0–2.
- *Length.*—Variable, ranges from 10 to 15 mm.
- *Width.*—Variable, ranges from 2 to 8 mm.
- *Overall shape.*—Often filiform (threadlike), narrow and nearly obovate petal-shape, possibly curled or deformed.
- *Apex shape.*—Pointed, acute to rounded.
- *Base shape.*—Acute.
- *Margin.*—Entire.
- *Color of upper petaloids.*—Red-purple group, RHS 58 C.
- *Color of lower petaloids.*—Red-purple group, RHS 58 C to RHS 65 A.

Petals:
- *Number of petals.*—Mostly 10–14.
- *Shape of petals.*—Obovate, base acute or attenuate, upper end is rounded, margin is entire.
- *Size of petals.*—Upper petals: 34 mm long, 17–18 mm wide. Lower petals: 29–30 mm long, 16–18 mm wide.
- *Color (general tonality from a distance of three meters).*—Pink.
- *Color of upper petals.*—Red-purple group, closest to RHS 58 C.
- *Markings of upper petals.*—2 dark red veins, RHS 53 A, surrounding a light pink stripe (RHS 55 B), and with a small violet (red-purple), RHS N74 A, spot in the middle of the petal.
- *Color of lower petals.*—Red-purple group, closest to RHS 61 D.
- *Markings of lower petals.*—Usually none, very fine dark red veins, RHS 53 B, may occur.
- *Color of lower surface of petals.*—Mainly red-purple, RHS 58 D, lower side of the upper petals is mainly red, RHS 52 C.

Sepals:
- *Number of sepals.*—5.
- *Shape of sepals.*—Linear to lanceolate, acute tip, truncate base, surface with weak pubescence, margin entire.
- *Size of sepals.*—15–17 mm long, 5 mm wide for the largest upper sepal, 4 mm in width for the other sepals.
- *Color of sepals.*—Mainly yellow-green, RHS 144 B (upper and lower surface); the largest sepal is mostly brown (greyed-red), from RHS 179 A (lower surface) to RHS 179 B (upper surface, inner).

Bud: (just prior to petals unfolding):
- *Shape.*—Elliptical, relatively long buds.
- *Color of sepals.*—Yellow-green, RHS 144 B.

*Color of petals.*—Light red in color, between RHS 52 A and RHS 52 B color designations.

*Length.*—28 mm.

*Width.*—11 mm.

Reproductive organs:

*Androecium.*—5–7 fertile anthers, moderate pollen, orange, RHS 25 A, filaments white, RHS 155 D, to light-pink, RHS 55 B.

*Gynoecium.*—One pistil, stigma 5–6-lobed, style and stigma pink, RHS 53 D.

*Fertility/seed set.*—Spontaneous seed set is only occasionally developed, from late summer to fall.

*Fruit.*—Oblong, about 5–6 mm wide, rostrum (beak) 42–46 mm long.

*Seed.*—Oblong, 4–5 mm long, brown (greyed-orange), RHS 177 B.

Spring flowering response period: In Hillscheid, Germany, in 2003 plants had on average 0.7 flowers opened 12 weeks after planting of rooted cuttings (pinched plants).

Outdoor flower production: Continuously and rich flowering, the flower count in 2003 in Hillscheid, Germany, indicated about 30 inflorescence per plant in late summer.

Durability: Fair stability of flower color, some fading may occur, fair rain resistance.

Lastingness of the individual flower: About 7 days at 18° C.

Fragrance: None.

Plant:

Foliage:

*Shape.*—Ivy-shaped, with cordate base, with the gap between the lowest lobes closed to overlapping, apex rounded with distinct lobes.

*Margin.*—Partly entire, some notches may occur near the tips of lobes.

*Texture.*—Upper surface smooth, slightly glossy.

*Size of leaf.*—92 mm wide, about 55 mm long.

*Color of upper surface.*—Medium green, closest to RHS 137 C.

*Color of zonation.*—Brown (greyed-orange), closest to RHS 166 A, medium distinct zonation (was evaluated as 4, in a range from 1 — invisible or very weak to 9 — very strong).

*Color of lower surface.*—Green, RHS 143 C.

*Petiole.*—40 mm long, 2–3 mm diameter, light green in color, RHS 143 C.

General appearance and form:

*Stem color.*—Light green, RHS 143 B.

*Internode length.*—40–45 mm.

*Branching pattern.*—8.5 branches on average.

*Size of plants.*—Height: 18.8 cm (15 week-old plants, as described). Diameter: 36 cm. Length: 20 cm (15 week-old plants). 71 cm (30 week-old plants, around September 1), measured from the top of the soil (base of the main stem) to the tips of the branches, without inflorescences.

I claim:

1. A new and distinct cultivar of *geranium* plant named 'Fiswipink', as described and illustrated herein.

* * * * *